United States Patent [19]

Hamprecht

[11] Patent Number: 4,522,763
[45] Date of Patent: Jun. 11, 1985

[54] N-ALKOXYCARBONYL- AND N-ALKOXYTHIOCARBONYL-AMIDINES AND THEIR PREPARATION

[75] Inventor: Gerhard Hamprecht, Weinheim, Fed. Rep. of Germany

[73] Assignee: BASF Aktiengesellschaft, Ludwigshafen, Fed. Rep. of Germany

[21] Appl. No.: 398,421

[22] Filed: Jul. 14, 1982

[30] Foreign Application Priority Data

Aug. 28, 1981 [DE] Fed. Rep. of Germany ....... 3134144

[51] Int. Cl.$^3$ ................. C07C 155/02; C07C 125/06; C07C 125/04
[52] U.S. Cl. ................. 260/455 A; 560/132; 560/115; 560/157; 544/7; 71/93
[58] Field of Search ............. 260/455 A; 560/24, 132, 560/115, 157

[56] References Cited

PUBLICATIONS

Reid, Organic Chemistry of Bivalent Sulfur, vol. IV, Chem. Pub. Co., Inc., 1962, p. 199.
Robertson et al., Laboratory Practice of Organic Chemistry, 4th Edition, (1962), MacMillan Company, New York, pp. 252–253.
Weissberger, Technique of Organic Chemistry, vol. 1, Physical Methods, Part I, Interscience Publishers, Inc., N.Y., 1959, pp. 662–663.
Noller, Textbook of Organic Chemistry, W. B. Saunders Co., Philadelphia, 2nd Ed., 1958, pp. 128–129.
Ann. 291, 372,373.
Z. Physik. Chem., 60 (1907), 385.
Z.f. Electrochemie, 23 (1917), 194.
M. Davies et al., Chem. and Ind. (1958), 628.

*Primary Examiner*—Henry R. Jiles
*Assistant Examiner*—Robert C. Whittenbaugh
*Attorney, Agent, or Firm*—John H. Shurtleff

[57] ABSTRACT

Novel N-alkoxycarbonyl- and N-alkoxythiocarbonyl-amidines and a process for the preparation of alkoxycarbonyl- and alkoxythiocarbonyl- amidines by reacting an amidine with an ester of chlorocarbonic acid or chlorothiocarbonic acid in the presence of an inorganic acid acceptor and a 2-phase aqueous/organic solvent mixture at from 0° to 60°0 C.

The novel end products which can be prepared by this process are useful starting materials for crop protection agents, and can be used in particular for the preparation of novel, selective herbicides.

28 Claims, No Drawings

N-ALKOXYCARBONYL- AND N-ALKOXYTHIOCARBONYL-AMIDINES AND THEIR PREPARATION

The present invention relates to novel N-alkoxycarbonyl- and N-alkoxythiocarbonyl-amidines and a process for the preparation of alkoxycarbonyl- and alkoxythiocarbonyl-amidines by reacting an amidine with an ester of chlorocarbonic acid or chlorothiocarbonic acid in the presence of an inorganic acid acceptor and a 2-phase aqueous/organic solvent mixture at from 0° to 60° C.

Ber. 23 (1890), 2919 discloses the preparation of ethoxycarbonylbenzamidine by reacting free benzamidine with ethyl chlorocarbonate in aqueous alkaline solution. The benzamidine must first be reacted with half of the theoretical amount of chlorocarbonate, and a further quantity of end product can be obtained from the filtrate by adding more sodium hydroxide solution and then more chlorocarbonate, but no yields are given. This process cannot be used for alkylamidines, since they decompose very rapidly in aqueous solution (S. Patai, The chemistry of amidines and imidates, J. Wiley & Sons, 1975, page 350), while phenyl substituents have a stabilizing effect.

When using an organic solvent and base, H. L. Wheeler et al. obtained only a diacylated product in the case of N-phenyl-phenylacetamidine, in spite of the use of stoichiometric amounts of pyridine and benzoyl chloride (J. Amer. Chem. Soc. 25 (1903), 796).

The same paper (page 795) reports that the acylation gave unsatisfactory yields since the decomposition products formed impeded isolation of the acylamidines. The reaction of free amidine with benzoyl chloride in ether in the absence of a base was described as, relatively, the best method, but here half of the amidine is lost and the end products have to be purified by recrystallization.

S. P. Joshi et al., J. Chem. Soc. (1936), 793–797 disclose condensation of ethyl chlorocarbonate with N,N'-di-m-nitrophenylbenzamidine in benzene in the presence of sodium bicarbonate over a period of 12 hours, but a yield of only 48.5% of monoacylated crude product is obtained, and this must also be recrystallized.

In view of the reaction conditions, all the conventional processes are unsatisfactory in respect of simple and economical procedure, particularly on an industrial scale.

We have found that N-alkoxycarbonyl- or N-alkoxythiocarbonyl-amidines of the formula

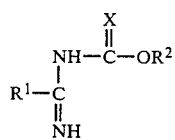

where $R^1$ is hydrogen or an aliphatic, cycloaliphatic or araliphatic radical, $R^2$ is an aliphatic radical and X is oxygen or sulfur, are obtained in an advantageous manner by a process wherein an amidine of the formula

where $R^1$ has the above meanings, or an amidine salt thereof, is reacted with an ester of chlorocarbonic acid or chlorothiocarbonic acid of the formula

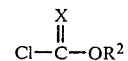

where $R^2$ and X have the above meanings, in the presence of an inorganic acid acceptor and a 2-phase aqueous/organic solvent mixture at from 0° to 60° C.

We have also found the novel N-alkoxycarbonyl- and N-alkoxythiocarbonyl-amidines of the formula

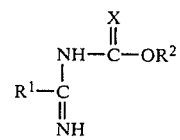

where $R^1$ is hydrogen or an aliphatic, cycloaliphatic or araliphatic radical, $R^2$ is an aliphatic radical and X is oxygen or sulfur.

If propionamidine and ethyl chlorocarbonate are used as starting materials, the course of the reaction can be represented by the following equation:

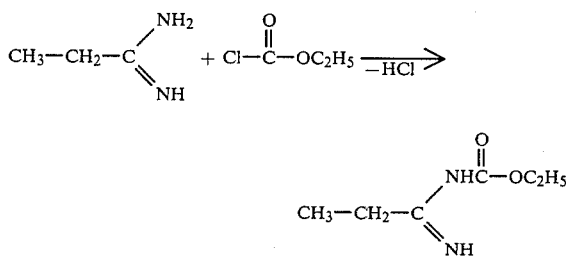

Compared to the prior art, the process according to the invention gives a better yield of purer alkoxycarbonyl- and alkoxythiocarbonyl-amidines in a simpler and more economical manner. Moreover, in spite of the presence of water, substantially no hydrolysis of the starting materials II or III occurs under the conditions according to the invention. Likewise, no diacylation is observed under the conditions according to the invention. The process can be carried out in particular with unsubstituted, unstable alkylamidines. In view of the prior art, all these advantageous properties are surprising.

Preferred starting materials II and III and, accordingly, preferred end products I are those where $R^1$ is hydrogen, or is alkyl of 1 to 10, in particular 1 to 6, carbon atoms which is unsubstituted or substituted by halogen, in particular bromine or chlorine, or by alkoxy or alkylmercapto where alkyl is in each case of 1 to 4 carbon atoms, or is alkenyl or alkynyl of 2 to 10, in particular 2 to 6, carbon atoms which is unsubstituted or substituted by halogen, in particular bromine or chlorine, or by alkoxy or alkylmercapto where alkyl is in each case of 1 to 4 carbon atoms, or is cycloalkyl of 3 to 7 carbon atoms, or is aralkyl of 7 to 12 carbon atoms which is unsubstituted or substituted by halogen, in particular bromine or chlorine, $R^2$ is alkyl of 1 to 5 carbon atoms and X is oxygen or sulfur. The aliphatic radicals can be straightchain or branched. The cycloaliphatic radicals can be cycloaliphatic rings which are unsubstituted or substituted by an aliphatic chain carrying the amidine radical. The above radicals can be further substituted by groups which are inert under the reaction conditions, e.g. alkyl or alkoxy, or alkylmercapto of 1 to 4 carbon atoms. The reaction is carried out with stoichiometric amounts of the starting materials II and III or an excess of one or other of the components, preferably with from 0.8 to 1.2, in particular from 1 to 1.1, moles of starting material III per mole of starting material II.

Examples of suitable amidines II include formamidine, acetamidine, propionamidine, butyramidine, isobutyramidine, valeramidine, isovaleramidine, sec.-valeramidine, pivalamidine, caproamidine, α-methylvaleramidine, enanthamidine, pelargonamidine, capramidine, propenamidine, propynamidine, but-2-en-4-amidine

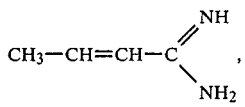

but-1-en-4-amidine, but-1-yn-4-amidine, but-2-yn-4-amidine, cyclopropylmethanamidine, cyclopentylmethanamidine, cyclohexylmethanamidine, cycloheptylmethanamidine, chloroacetamidine, α-chloropropionamidine, β-chloropropionamidine, methoxyacetamidine, α-methoxypropionamidine, β-methoxypropionamidine, α-methylmercaptopropionamidine, β-methylmercaptopropionamidine, phenylethanamidine, 2-chlorophenylethanamidine, 3-chlorophenylethanamidine, 4-chlorophenylethanamidine, 3,4-dichlorophenylethanamidine and 2,4-dichlorophenylethanamidine.

Examples of starting materials of the formula III are methyl chloroformate, ethyl chloroformate, propyl chloroformate, isopropyl chloroformate, O-methyl thiocarbonate chloride and O-ethyl thiocarbonate chloride.

The reaction is carried out at from 0° to 60° C., preferably from 10° to 30° C., under atmospheric or superatmospheric pressure, continuously or batchwise.

Advantageously, the reaction is carried out by adding the starting material III to the starting material II, or a salt thereof, and an organic solvent which is inert under the reaction conditions, in the presence of water. Particularly suitable organic solvents are aliphatic chlorohydrocarbons, e.g. tetrachloroethylene, 1,1,2,2- and 1,1,1,2-tetrachloroethane, dichloropropane, methylene chloride, dichlorobutane, chloroform, carbon tetrachloride, 1,1,1- and 1,1,2-trichloroethane, trichloroethylene, pentachloroethane, 1,2-dichloroethane, 1,1-dichloroethane and 1,2-cis-dichloroethylene; aromatic chlorohydrocarbons, e.g. chlorobenzene, fluorobenzene, bromobenzene, iodobenzene, o-, m- and p-dichlorobenzene, o-, m- and p-dibromobenzene, o-, m- and p-difluorobenzene, o-, m- and p-chlorotoluene, 1,2,4-trichlorobenzene, chloronaphthalene and dichloronaphthalene; ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, thioanisole and β,β'-dichlorodiethyl ether; nitrohydrocarbons, e.g. nitromethane, nitroethane, nitrobenzene, o-, m- and p-chloronitrobenzene and o-nitrotoluene; nitriles, e.g. acetonitrile, butyronitrile, isobutyronitrile, benzonitrile and m-chlorobenzonitrile, aliphatic or cycloaliphatic hydrocarbons, eg. heptane, pinane, nonane, o-, m- and p-cymene, gasoline fractions within a boiling point range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, e.g. 2-ethylhexanoic acid dimethylamide; aromatic hydrocarbons, e.g. toluene and xylene; and appropriate mixtures. Advantageously, from 100 to 2,000% by weight, preferably from 200 to 1,000% by weight, based on the starting material II, of the solvent mixture is used, the solvent containing from 10 to 50% by weight, preferably from 20 to 40% by weight, of water.

Preferred acid acceptors which may be used are compounds of zinc, alkali metals and alkaline earth metals, advantageously hydroxides, carbonates, bicarbonates, oxides, acetates and formates, and appropriate mixtures, and examples include potassium hydroxide, sodium hydroxide, sodium carbonate, potassium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate and sodium acetate.

Advantageously, an equivalent amount or excess of not more than 20%, based on the amidine of the formula II, of acid acceptor is used. In a preferred form of the process according to the invention, however, a salt of the amidine is used directly, in which case an excess of not more than 120% by weight, based on the amidine II, of the acid acceptor is advantageously used, and the amidine of the formula II, employed in the reaction, is liberated directly under the reaction conditions.

The process is advantageously carried out by running the starting material III and the equivalent amount of aqueous acid acceptor through two inlets into an approximately equivalent amount of amidine of the formula II in an inert organic solvent, at the reaction temperature. In the preferred case where an amidine salt is used, two moles of acid acceptor per mole of starting material II are advantageously used.

However, it is also possible to run a mixture of the starting material II or its salt in an inert organic solvent or in water, and, via a second inlet, the aqueous acid acceptor, into a solution of the starting material III in an inert organic solvent at from 0° to 60° C., preferably from 10° to 30° C. The reaction is brought to completion by stirring the mixture at from 0° to 60° C., preferably from 10° to 30° C., for a further 2 minutes to 6 hours.

The reaction mixture is worked up by filtering off with suction any neutralization salt which has precipitated and separating off the organic phase from the filtrate. The organic phase is extracted again with water, if necessary, and then dried, or concentrated directly. The desired end products are obtained in a pure form, and if necessary they can be purified by recrystallization. However, since very pure crude products are obtained, in most cases they do not have to be isolated and their solution can be used directly for further reactions.

As compounds in equilibrium, the invention embraces, in addition to the end products of the formula I, their tautomeric forms of the formula Ia.

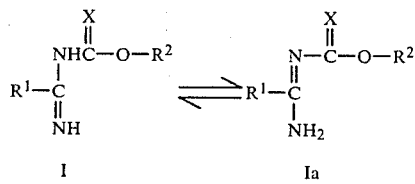

The novel end products which can thus be prepared according to the invention are useful starting materials for crop protection agents, and are particularly suitable for the preparation of novel, selective herbicides. For example, they can be converted into substituted 2H-1,2,4,6-thiatriazin-3-one 1,1-dioxides by means of an aminosulfonyl chloride and cyclization. These products are themselves herbicides, or can be converted by means of halogenating agents into 3-halo-2H-1,2,4,6-thiatriazine 1,1-dioxides. These latter products also have a herbicidal action or can be converted into novel substituted 2H-1,2,4,6-thiatriazine 1,1-dioxides having an excellent herbicidal action.

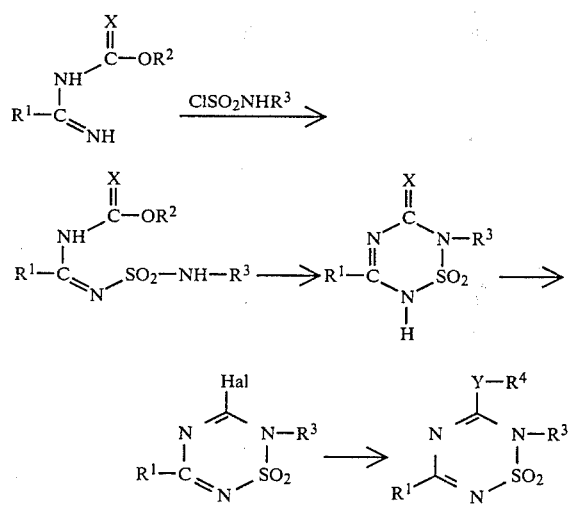

In the Examples which follow, parts are by weight.

EXAMPLE 1

(a) Comparative Example 80 parts of 50% strength sodium hydroxide solution are added at 25° C. to a solution of 94.5 parts of acetamidinium chloride in 400 parts of water, while stirring. 47.3 parts of methyl chloroformate are then added at the same temperature in the course of 10 minutes, while stirring, and stirring is continued for 10 minutes. Another 80 parts of 50% strength sodium hydroxide solution and 47.3 parts of methyl chloroformate are then added under the same conditions. After the reaction mixture has been stirred for a further 10 minutes, it is extracted with three times 130 parts of methylene chloride. The organic phase is concentrated to give 13 parts (=11% of theory) of N-methoxycarbonylacetamidine of melting point 105°–110° C.

(b) (According to the invention)

23 parts of methyl chloroformate and 36.5 parts of 50% strength sodium hydroxide solution are added at from 18° to 20° C. to a mixture of 20 parts of acetamidine hydrochloride in 120 parts of methyl tert.-butyl ether and 20 parts of water in the course of 20 minutes, while stirring. The mixture is stirred at 20° C. for 20 minutes, the phases are separated and the aqueous phase is extracted again with twice 40 parts of methyl tert.-butyl ether. The organic extract is concentrated under reduced pressure to give 15 parts (=60.8% of theory) of N-methoxycarbonylacetamidine of melting point 120°–125° C.

EXAMPLE 2

222 parts of methyl chloroformate and 337 parts of 50% strength sodium hydroxide solution are added via two inlets to a mixture of 286 parts of butyramidine hydrochloride in 1,300 parts of methylene chloride and 500 parts of water, at from 10° to 15° C., in the course of 25 minutes, while stirring. The mixture is stirred at room temperature for 2 hours, and the organic phase is separated off and concentrated on a rotary evaporator to give 320 parts (95% of theory) of N-methoxycarbonylbutyramidine of $n_D^{25}$ 1.4763.

EXAMPLE 3

(a) 298.6 parts of methyl chloroformate and 472.8 parts of 50% strength sodium hydroxide solution are added via two inlets to a mixture of 298 parts of propionamidine hydrochloride in 1,300 parts of methylene chloride and 200 parts of water, at from 20° to 25° C., in the course of 25 minutes, while stirring. The reaction mixture is stirred at 25° C. for three hours and diluted with 300 parts of water, and the phases are separated. The aqueous phase is extracted once with 200 parts of methyl chloride and the solvent is stripped off from the organic extract to give 325 parts (=91% of theory) of N-methoxycarbonylpropionamidine of melting point 87°–93° C.

(b) The same product is obtained in the same yield and purity under the same reaction conditions but using 1,300 parts of ethyl acetate and stirring the mixture for 30 minutes.

EXAMPLE 4

165 parts of methyl chloroformate and 141.8 parts of sodium hydroxide in 590 parts of water are added via two inlets to 221 parts of 2-methylpropionamidine hydrochloride in 1,000 parts of diethyl ether, at from 25° to 30° C., in the course of 40 minutes, while stirring. The mixture is stirred at room temperature for one hour, and the organic phase is separated off. The aqueous phase is extracted again with 200 parts of diethyl ether, and the solvent is removed from the combined organic extracts to give 223 parts (86% of theory) of N-methoxycarbonyl-2-methylpropionamidine of melting point 127°–130° C.

EXAMPLE 5

137.2 parts of methyl chloroformate and a solution of 162.7 parts of potassium hydroxide in 180 parts of water are added via two inlets to a mixture of 246 parts of benzylmethanamidine hydrochloride in 530 parts of 1,2-dichloroethane and 85 parts of water, at from 10° to 15° C., in the course of 35 minutes. The mixture is stirred at 25° C. for 20 minutes, the organic phase is separated off and the aqueous phase is extracted twice more with 1,2-dichloroethane. The organic extracts are concentrated to give 259.8 parts (93% of theory) of N-methoxycarbonylbenzylmethanamidine of $n_D^{25}$ 1.5247.

EXAMPLE 6

78.8 parts of methyl chloroformate and a mixture of 46.8 parts of potassium hydroxide in 215 parts of water are added via two inlets to a mixture of 113.8 parts of isovaleramidine hydrochloride in 530 parts of methylene chloride, at from 0° to 10° C., in the course of 25 minutes, while stirring. The mixture is stirred at 25° C. for 30 minutes, the phases are separated and the aqueous phase is extracted once with methylene chloride. The solvent is removed from the organic extract to give 123 parts (93.3% of theory) of N-methoxycarbonylisovaleramidine of melting point 82°–86° C.

EXAMPLE 7

123 parts of ethyl chloroformate and 170.4 parts of 50% strength sodium hydroxide solution are added via two inlets to a mixture of 94.6 parts of acetamidine hydrochloride in 750 parts of methylene chloride and 250 parts of water, at from 10° to 15° C., in the course of 30 minutes, while stirring. After the mixture has been stirred at 25° C. for 15 minutes, the phases are separated. The aqueous phase is extracted with twice 100 parts of methylene chloride, and the solvent is removed from the organic extract to give 93.4 parts (72% of theory) of N-ethoxycarbonylacetamidine of melting point 111°–114° C.

The Examples which follow are obtained by a procedure similar to that in Example 2:

| Example | $R^1-\underset{\underset{NH_2}{\|}}{C}=NH \cdot HCl$ Parts of $R^1$ | | Parts of $Cl-\overset{O}{\overset{\|}{C}}OCH_3$ | Parts of 50% strength NaOH | $R^1-\underset{\underset{NH_2}{\|}}{C}=N-CO_2CH_3$ Parts of $R^1$ | | a b Melting point/$n_D^{25}$ | Yield in % of theory |
|---|---|---|---|---|---|---|---|---|
| 8 | 64.5 | $Cl-CH_2$ | 53.5 | 92.8 | 45.1 | $Cl-CH_2$ | (a) 94–97° C. | 60 |
| 9 | 67 | $CH_3-O-CH_2CH_2-$ | 45.8 | 78 | 59 | $CH_3-O-CH_2CH_2-$ | (b) 1.4735 | 76.4 |

We claim:

1. A process for the preparation of an N-alkoxycarbonyl- or N-alkoxythiocarbonyl-amidine of the formula

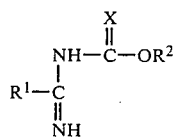

where $R^1$ is hydrogen or an aliphatic, cycloaliphatic or araliphatic radical, $R^2$ is an aliphatic radical and X is oxygen or sulfur, wherein an amidine of the formula

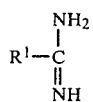

where $R^1$ has the above meanings, or an amidine salt thereof, is reacted with an ester of chlorocarbonic acid or chlorothiocarbonic acid of the formula

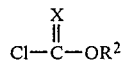

where $R^2$ and X have the above meanings, in the presence of an inorganic acid acceptor and a 2-phase mixture of water and organic solvent at from 0° to 60° C.

2. An N-alkoxycarbonyl- or N-alkoxythiocarbonylamidine of the formula

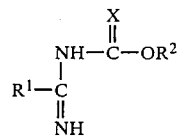

where $R^1$ is hydrogen or a $C_1$-to-$C_{16}$ aliphatic, cycloaliphatic or araliphatic radical, $R^2$ is a $C_1$-to-$C_5$ aliphatic radical and X is oxygen or sulfur.

3. A process as claimed in claim 1, wherein the reaction is carried out with from 0.8 to 1.2 moles of starting material III per mole of starting material II.

4. A process as claimed in claim 1, wherein the reaction is carried out at from 10° to 30° C.

5. A process as claimed in claim 1, wherein the reaction is carried out with from 100 to 2,000% by weight, based on the starting material II, of the solvent mixture.

6. A process as claimed in claim 1, wherein the reaction is carried out with a solvent containing from 10 to 50% by weight of water.

7. A process as claimed in claim 1, wherein the reaction is carried out with a zinc, alkali metal or alkaline earth metal compound in the form of a hydroxide, carbonate, bicarbonate, oxide, acetate or formate, as the acid acceptor.

8. A process as claimed in claim 1, wherein the reaction is carried out in an equivalent amount or an excess of not more than 20% by weight of acid acceptor, based on the amidine of the formula II.

9. A process as claimed in claim 1, wherein the reaction is carried out with an excess of not more than 120% by weight of acid acceptor, based on the amidine II, if the salt of the amidine is used.

10. A compound as claimed in claim 2 wherein:
$R^1$ is selected from the group consisting of
hydrogen,
alkyl of 1 to 10 carbon atoms, alkenyl of 2 to 10 carbon atoms, alkynyl of 2 to 10 carbon atoms, each of said alkyl, alkenyl and alkynyl being unsubstituted or substituted by halogen or by alkoxy or alkylmercapto of 1 to 4 carbon atoms each;
cycloalkyl of 3 to 7 carbon atoms and aralykyl of 7 to 12 carbon atoms, each of said cycloalkyl and aralkyl being unsubstituted or substituted by halogen or by alkyl, alkoxy or alkylmercapto of 1 to 4 carbon atoms each;
$R^2$ is alkyl of 1 to 5 carbon atoms; and X is oxygen or sulfur.

11. A process as claimed in claim 1 wherein the organic solvent is selected from the group consisting of aliphatic, cycloaliphatic and aromatic hydrocarbons which may be unsubstituted or substituted with the proviso that the solvent is inert under the reaction conditions.

12. A process as claimed in claim 11 wherein the organic solvent is methyl tert.-butyl ether.

13. A process as claimed in claim 11 wherein the organic solvent is methylene chloride.

14. A process as claimed in claim 11 wherein the organic solvent is ethyl acetate.

15. A process as claimed in claim 11 wherein the organic solvent is diethyl ether.

16. A process as claimed in claim 11 wherein the organic solvent is 1,2-dichloroethane.

17. A process as claimed in claim 5 wherein the reaction is carried out at a temperature of 10° to 30° C.

18. A process as claimed in claim 7 wherein the reaction is carried out at a temperature of 10° to 30° C.

19. A process as claimed in claim 11 wherein the reaction is carried out at a temperature of 10° to 30° C.

20. A process as claimed in claim 1 wherein the amidine II is selected from the group consisting of formadine, acetamidine, propionamidine, butyramidine, isobutyramidine, valeramidine, isovaleramidine, sec.-valeramidine, pivalamidine, caproamidine, α-methylvaleramidine, enanthamidine, pelargonamidine, capramidine, propenamidine, propynamidine, but-2-en-4-amidine, but-1en-4-amidine, but-1-yn-4-amidine, but-2-yn-4-amidine, cyclopropylmethanamidine, cyclopentylmethanamidine, cyclohexylmethanamidine, cycloheptylmethanamidine, chloroacetamidine, α-chloropropionamidine, β-chloropropionamidine, methoxyacetamidine, α-methoxypropionamidine, β-methoxypropionamidine, α-methylmercaptopropionamidine, β-methylmercaptopropionamidine, phenylethanamidine, 2-chlorophenylethanamidine, 3-chlorophenylethanamidine, 4-chlorophenylethanamidine, 3,4-dichlorophenylethanamidine and 2,4-dichlorophenylethanamidine.

21. A process as claimed in claim 1 wherein the starting ester III is selected from the group consisting of methyl chloroformate, ethyl chloroformate, propyl chloroformate, O-methyl thiocarbonate chloride and O-ethyl thiocarbonate chloride.

22. The compound of claim 10 which is N-methoxycarbonylacetamidine.

23. The compound of claim 10 which is N-methoxycarbonylbutyramidine.

24. The compound of claim 10 which is N-methoxycarbonylpropionamidine.

25. The compound of claim 10 which is N-methoxycarbonyl-2-methylpropionamidine.

26. The compound of claim 10 which is N-ethoxycarbonylacetamidine.

27. The compound of claim 10 which is N-methoxycarbonyl-chloroacetamidine.

28. The compound of claim 10 which is N-methoxycarbonyl-3-methoxypropioamidine.

* * * * *

UNITED STATES PATENT AND TRADEMARK OFFICE
CERTIFICATE OF CORRECTION

PATENT NO. : 4,522,763
DATED : June 11, 1985
INVENTOR(S) : Gerhard Hamprecht

It is certified that error appears in the above-identified patent and that said Letters Patent is hereby corrected as shown below:

In Claim 20, line 8, change "but-1en-4-amidine" to
-- but-1-en-4-amidine --.

Signed and Sealed this

Twenty-ninth Day of October 1985

[SEAL]

Attest:

DONALD J. QUIGG

Attesting Officer

Commissioner of Patents and
Trademarks—Designate